United States Patent [19]
Long et al.

[11] Patent Number: 5,745,238
[45] Date of Patent: Apr. 28, 1998

[54] APPARATUS AND METHOD FOR NON-DESTRUCTIVE INSPECTION AND/OR MEASUREMENT

[75] Inventors: David Clifford Long, Wappingers Falls; John Blake Pavelka, Beacon, both of N.Y.; Karl Friedrich Stroms, Las Vegas, Nev.; Gerhard Weiss, deceased, late of LaGrangeville, N.Y., by Helga Weiss, Executrix

[73] Assignee: International Business Machines Corporation, Armonk, N.Y.

[21] Appl. No.: 995,258

[22] Filed: Dec. 22, 1992

[51] Int. Cl.$^6$ ..................................... G01N 21/17
[52] U.S. Cl. .............................. 356/376; 356/371
[58] Field of Search ................... 356/372, 375, 356/376, 371, 394, 398, 237, 239, 445, 446; 73/104, 800, 865.8; 250/571, 572, 559, 561, 562; 358/101, 106, 107

[56] References Cited

U.S. PATENT DOCUMENTS

| | | | |
|---|---|---|---|
| 3,185,022 | 5/1965 | Holeman. | |
| 3,767,306 | 10/1973 | Mast et al. | 356/102 |
| 4,194,127 | 3/1980 | Schmidt | 250/572 |
| 4,290,698 | 9/1981 | Milana | 356/371 |
| 4,332,477 | 6/1982 | Sato | 356/371 |
| 4,664,514 | 5/1987 | Corby, Jr. | 356/36 |
| 4,730,927 | 3/1988 | Ototake | 356/371 |
| 4,803,871 | 2/1989 | Harada et al. | 73/104 |
| 5,124,927 | 6/1992 | Hopewell et al. | 356/394 |
| 5,131,753 | 7/1992 | Pine et al. | 356/376 |
| 5,349,443 | 9/1994 | Guerra | 356/371 |

FOREIGN PATENT DOCUMENTS

| | | | |
|---|---|---|---|
| 2174608 | 7/1987 | Japan. | |
| 0099807 | 4/1990 | Japan | 356/371 |

*Primary Examiner*—Hoa Q. Pham
*Attorney, Agent, or Firm*—Aziz M. Ahsan

[57] ABSTRACT

The present invention relates generally to a new apparatus and a method for non-destructive inspection and/or measurement. And, more particularly, the invention encompasses an apparatus that has a flexible foil or membrane secured thereto which conforms to the surface of the part that is being inspected and/or measured in a nondestructive manner using differential pressure.

74 Claims, 3 Drawing Sheets

APPARATUS AND METHOD FOR NON-DESTRUCTIVE INSPECTION AND/OR MEASUREMENT

FIELD OF THE INVENTION

The present invention relates generally to a new apparatus and a method for non-destructive inspection and/or measurement. And, more particularly, the invention encompasses an apparatus that has a flexible foil or membrane secured thereto which conforms to the surface of the part that is being inspected and/or measured in a nondestructive manner using differential pressure.

BACKGROUND OF THE INVENTION

In a manufacturing environment practically every product made is inspected. In some cases the part may just be visually inspected, and in others a more elaborate inspection method and apparatuses might be used. Some of the inspection methods used by the industry may have a detrimental effect on the item to be inspected, while others may provide a non-destructive method and an apparatus for such an inspection.

There are quite a number of methods and apparatuses for the inspection of parts or products, and some of them have been a subject of a patent while other have not. For example, J. M. Holeman (U.S. Pat. No. 3,185,022) obtained a patent for his optical gage for testing surface imperfections. He used a thin layer of an opaque material having a plurality of holes and secured it to a light transparent supporting member. This gage was then placed over the test piece, and rays of light were reflected off the gage and the test piece. The observer viewing the reflected light would see a dark area on the testing device which corresponds to the position of the defects.

Another patent was obtained by Mast et al. (U.S. Pat. No. 3,767,306). Mast et al. used a method that employed the surface tension of a liquid film to optically detect and measure the size of particulates. Their invention was operable only for planar surfaces and for specimens which could be exposed to a liquid film.

Corby, Jr., (U.S. Pat. No. 4,664,514) obtained a patent for a method of enhancing surface features and detecting the same. He disclosed that the optical properties of the surface to be inspected could be enhanced by depositing a thin coating of a solid film over the part to be tested. This could be done using vapor condensation, such as sputtering, evaporation or gas disassociation. The thin solid film could be either highly reflective or highly absorptive. Portions of the solid thin film are then removed from the surface, for example, by abrasion, while the remaining coating material is in a pattern depending on anomalies. The surface is then irradiated and inspected under light and the differential reflection between the remaining coating material and the surface itself enhances the visibility of surface characteristics.

Akira Sase in Japanese Patent Publication No. 62-174,608, disclosed the use of a flexible film that is under force of air pressure to flatten a warped, twisted or bent part and hold the part flat while the part is being inspected.

However, the present invention discloses methods and apparatuses for inspection of parts that do not damage or destroy the part to be inspected. This is done by providing an apparatus having a flexible foil secured thereto, and this flexible foil is brought in contact with the part to be inspected. If the part can be exposed to vacuum and can fit inside the novel fixture then the part to be inspected is secured inside the fixture and vacuum is obtained. The flexible foil will now temporarily conform to the surface of the part to be inspected and then using a standard optical or opto-electronic method or tools the part can be inspected.

For cases where the part to be inspected is too large or that it cannot be exposed to vacuum, then for those situations the apparatus having the flexible foil is placed over the part to be inspected and through differential pressure the flexible foil is forced to temporarily conform to the surface of the part and then using standard opto-electronic or optical methods and tools the part can now be inspected.

PURPOSES AND SUMMARY OF THE INVENTION

The invention is a novel method and an apparatus for non-destructive inspection and/or measurement. More particularly, the invention encompasses an apparatus that has a flexible foil or membrane secured thereto, in which a portion of the membrane conforms to the surface of the part that is being inspected and/or measured in a nondestructive manner. And, then using standard inspection techniques and tools the surface of the membrane that is conforming to the part is inspected.

Therefore, one purpose of this invention is to provide an apparatus and a method that will provide the needed surface inspection and/or measurement of a part without damaging or destroying the part.

Another purpose of this invention is to provide a fixture with a flexible foil or membrane that will temporarily conform to the surface of the part during inspection and/or measurement.

Still another purpose of this invention is to have flexible foil or membrane that will reflect light during inspection and/or measurement of the part.

Yet another purpose of this invention is to have flexible foil or membrane that will absorb light during inspection and/or measurement of the part.

Still yet another purpose of this invention is to have the flexible foil or membrane conform exactly to the surface to be inspected and/or measured without distorting or disturbing the original topology.

Yet another purpose of this invention is to change the optical properties of the surface to be inspected by translating the optical properties of the flexible film to the surface to be inspected and/or measured.

Still another purpose of this invention is to use a flexible foil or membrane that locally change their optical and/or physical properties as a result of some external influence, such as a change in color in response to local temperature change.

Yet another purpose of this invention is to cause differential pressure across the flexible foil during inspection and/or measurement using a fluid, such as, air, water, mineral oils, Freon, etc.

In one aspect this invention comprises a method for the inspection and/or measurement of surfaces, comprising:

(a) securing at least one flexible membrane to a housing, said flexible membrane having opposed surfaces, (b) at least one means to create and maintain a pressure differential between said opposed surfaces of said at least one flexible membrane, so that at least a portion of said flexible membrane is in conformal contact with at least a portion of said surfaces to be inspected and/or measured, (c) at least one inspection means to inspect at least a portion of the surface of said flexible membrane that is in conformal contact with said surfaces to be inspected while said pressure differential is maintained across said at least one flexible membrane.

In another aspect this invention comprises an apparatus for the inspection and/or measurement of surfaces, comprising:

(a) at least one housing having at least one flexible membrane secured to said housing, said flexible membrane having opposed surfaces, (b) at least one means to create and maintain a pressure differential between said opposed surfaces of said at least one flexible membrane, so that at least a portion of said flexible membrane is in conformal contact with at least a portion of said surfaces to be inspected and/or measured, (c) at least one inspection means to inspect at least a portion of the surface of said flexible membrane that is in conformal contact with said surface to be inspected while said pressure differential is maintained across said at least one flexible membrane.

BRIEF DESCRIPTION OF THE DRAWINGS

The features of the invention believed to be novel and the elements characteristic of the invention are set forth with particularity in the appended claims. The figures are for illustration purposes only and are not drawn to scale. The invention itself, however, both as to organization and method of operation, may best be understood by reference to the detailed description which follows taken in conjunction with the accompanying drawings in which:

DETAILED DESCRIPTION OF THE INVENTION

Preferred embodiments of the present invention are depicted in FIGS. 1–4 and 6, in which like numerals refer to like features of the invention. Such features are not necessarily shown to scale in the drawings.

The invention disclosed here in one aspect is a method and an apparatus for temporarily enhancing the optical properties of the surface of an object to be inspected and/or measured. Hereinafter for the ease of discussion the term inspection will be used to describe the novel process of inspection and/or measurement.

The method and the apparatus of this invention allows standard optical inspection and measurement techniques and/or tools to be used on specimens where the original surface of the specimen is not optically suitable for such inspection and/or measurement. The method and the apparatus provides a means, such as a flexible foil or a membrane, to conformally follow the surface contours of the surface to be inspected without distorting or damaging the original physical surface topology.

With this invention different types of flexible foils or membranes could be used, for example, a transparent or a reflective or a translucent flexible foil could Me used. A transparent foil has the added advantage of not obscuring the view of the surface to be inspected.

Additionally, "smart films" can be used with this invention. Smart films are films or foils or membranes in which at least a portion of the flexible film or membrane changes its optical or physical characteristic under an external influence. This external influence could be thermal, mechanical, optical, chemical, electrical, magnetic, piezo-electric, etc.

Furthermore, the flexible foil or membrane could be a single layered material or could comprise of multi-layered films. Or, for example, the flexible foil could be formed by sandwiching a fluidic material between two or more layers, such as liquid crystal films.

Other types of membranes and printed patterns, not described here, may also be used to suit a specific application, such as, transparent or opaque colored films or polarizing films or films having diffraction patterns or holographic films, etc..

Additionally, either broad band or narrow band optical coatings could also be applied to at least one surface of the film or membrane. These films could also contain optical filters. These unique types of films are typically selected to enhance the viewing, inspection or measurement of the part.

For some applications, where the flexible film or membrane does not make proper and/or complete contact with the part or the surface to be inspected and/or measured, at least a portion of the surface of the flexible membrane could be physically modified, such as, by forming micro-channels on the surface or frosting the surface or providing surface porosity or surface roughness, or sand blasting the surface, etc.. This surface modification could be introduced onto at least one surface of the film to allow any entrapped fluid, such as, gas, air, etc., to escape in order to create a better temporary contact between the film and the part or surface to be inspected and/or measured. It would be preferred that this modified surface of the membrane be on the side that comes in physical contact with the surface or part to be inspected and/or measured.

Therefore the flexible membrane could be selected from a group comprising piezo electric membrane, temperature sensitive membrane, strain sensitive membrane, stress sensitive membrane, polarizing membrane, holographic membrane, colored membrane, membrane having diffraction grating, reflective membrane, transparent membrane, membrane having at least one optical coating, membrane having at least one optical filter or membrane having at least one fluid sandwiched therein, to name a few. Additionally, a portion of the flexible membrane could have a rough surface, and this rough surface could be formed by either pores or micro-channels or sand blasting, etc..

One method of this invention strives to change the optical properties of the surface to be inspected by translating the optical properties of the flexible film to the surface to be inspected. This invention allows the enhancement of the optical properties of the surface to be inspected, such that the surface can be inspected by using any of the known or standard optical methods and/or tools.

Both reflective and non-reflective surfaces can be inspected using this invention as it is the properties of the flexible foil or membrane that assists in the inspection of the surface not the material or optical characteristics of the surface. The flexible foil or membrane only temporarily conforms to the surface of the part to be inspected, and therefore there is no residual effect on the parts that are inspected. The apparatus or the method could be linked to computer system, for example, to do automatic surface topology inspections or to be used in mass production inspections or data storage, etc..

Figure 1:
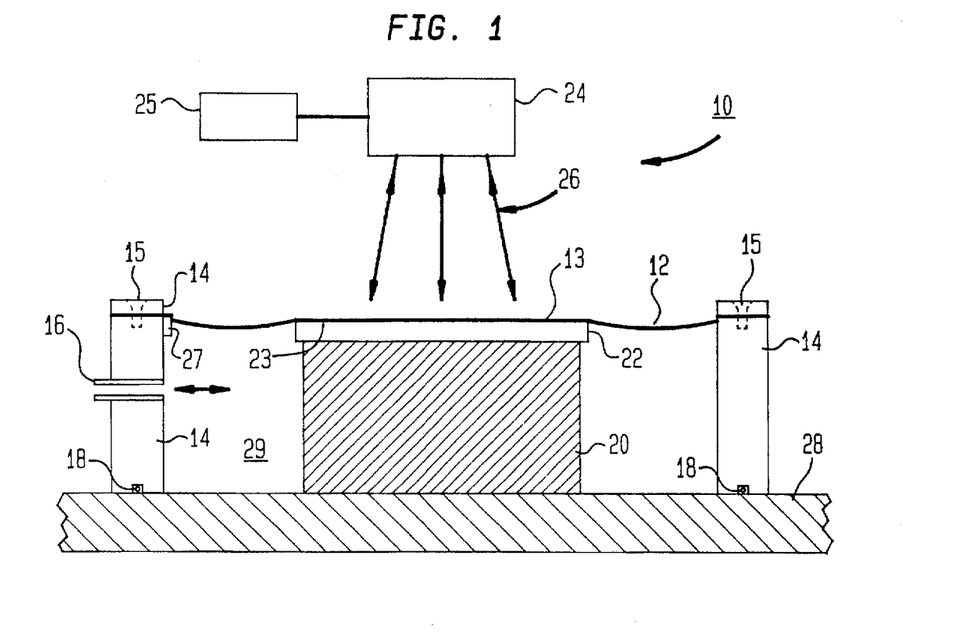
FIG. 1, illustrates one preferred embodiment of this invention.

One preferred embodiment of the apparatus 10, is shown in FIG. 1. The part or object to be inspected 22, having surface 23, is held in a suitable part or object holding fixture 20. This fixture 20, could rest on or be secured to a flat base 28. A foil or membrane fixture or frame 14, securely holds a flexible foil or membrane 12, using securing means 15. The peripheral edges of the foil or membrane 12, are preferably secured to the fixture or frame 14. The optical properties of the membrane 12, are chosen to meet the requirements of the inspection or measurement technique. A seal or gasket 18, is typically attached to the bottom of the frame 14, in order to provide an air- or fluid-tight seal during the inventive inspection process. One or more pressure or temperature sensor means 27, could be secured to the frame 14, or to the flexible membrane 12.

During the inspection process the frame 14, having the flexible membrane 12, is placed over the surface 23, of the object 22, while the frame 14, rests on the flat base 28, or is secured thereto. The frame 14, is designed so that, when the frame 14, is in place, the membrane 12, rests just slightly above the part to be inspected 22. It may be desirable that the part holding fixture 20, be adjustable so that parts 22, of different sizes can be accommodated.

Once the frame 14, is in place over the object 22, and resting firmly on the base 28, the air is evacuated from the chamber 29, through at least one vacuum or pressure port 16. The chamber 29, comprises the area or volume between the base 28, and the membrane 12. Differential pressure outside the frame 14, forces the membrane 12, into intimate contact with the general topology of the surface 23, of the object 22. Once in contact, the membrane 12, typically conforms to the surface 23, of the object 22. The surface 23, of the object 22, may now be inspected using any of the standard opto-electronic inspection systems 24, such as interferometers, auto-collimators, TV cameras, IR cameras, laser scanners, etc., to name a few. Care must be taken so as not to create too much vacuum inside the chamber 29, so as to rupture the flexible foil 12, or to create too little vacuum so that the flexible foil 12, does not conform to the surface contours of the part 22. Additionally, care must be taken at all times not to disturb or deform or damage the imaging or measuring surface 23, during the inspection and/or measurement process.

Once the chamber 29, is properly evacuated the imaging rays 26, from the inspection system 24, are allowed to reflect off the surface 13, in case of a reflective film 12, or to reflect off the surface 23, for a clear or transparent film 12, and the image that is received is then processed as desired, for example, the information could be stored into a data base or be used to compare one surface image with an image already stored in a data base or the image could be sent to another location for further processing. The inspection system 24, could be connected to one or more data storage or data retrieval or computer or controller systems 25.

Imaging rays 26, typically originate in the inspection system 24, and they strike the surface 13, of the membrane 12. The imaging rays 26, are then normally allowed to reflect back to the inspection system 24, where they are further processed and analyzed using standard industrial techniques.

During the inspection of the part 22, the part 22, could be powered-up or could be externally heated or cooled or mechanically stressed to further obtain useful information, such as, stress, strain, hidden cracks, defects, attributes or thermal properties of the part 22. The part 22, could also be thermally or mechanically cycled to expose any latent defects or other attributes.

Figure 2:
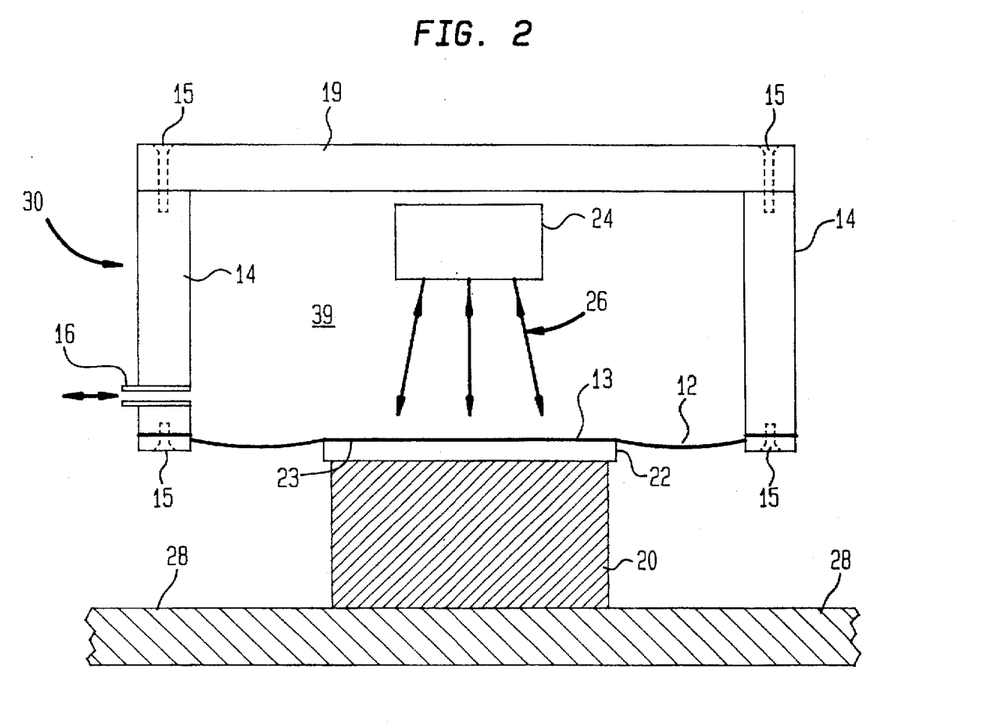
FIG. 2, illustrates another preferred embodiment of this invention.

Another preferred embodiment of the apparatus 30, of this invention is shown in FIG. 2, which is a self-contained unit 30. This configuration could be used in circumstances where it is desired to protect the optical surface of the membrane 12. It may also be used when obstructions surround the fixture 14, or when the base 28, is otherwise unsuitable to provide a sealing surface for gasket 18. In addition, a version of this configuration can be used when the object to be inspected 22, is larger than the frame 14, as shown more clearly in FIG. 3.

As shown in FIG. 2, the object to be inspected 22, is held in a fixture 20, that is secured to base 28. In this case, however, the frame 14, has been modified. The modified frame 14, normally securely holds the flexible membrane 12, and the standard opto-electronic inspection system 24. The cover 19, secured to the frame 14, could be made of a transparent material to act as a viewing window 19, or a portion of the cover 19, could have means that act as a viewing window. The frame 14, could also contain the inspection system 24, and this entire assembly could be constructed to be fluid-tight inside the chamber 39. The frame 14, would be positioned such that, as before, the membrane 22, rests just slightly above the surface 23, of the object to be inspected 22.

The chamber 39, would then be pressurized using a fluid, such as, air, water, Freon, mineral oil, etc., through port 16, so as to force the surface 13, of the membrane 12, into intimate contact with the surface 23, of the object 22. During this pressurization process care should be taken so as not to rupture the flexible membrane 12, by using too much fluid pressure, or using too little fluid pressure and not making the desired conformal contact with the surface 23, of the part 22. Additionally, care must be taken at all times not to deform or disturb or damage the imaging or measuring surface 23, during the inspection and/or measurement process.

Imaging rays 26, from the standard opto-electronic inspection system 24, are then allowed to strike the surface 13, of the membrane 12, and this translates the optical properties seen by the surface 13, of the membrane 12, to the surface 23, of object 22. The inspection/measurement apparatus 24, is then used to view the inspected image of the surface 23, of the object 22, through either the viewing window 19, or through an electronic type system 25 (not shown in FIG. 2).

An advantage of the embodiment 30, is that it is a self-contained system and therefore it reduces the probability of contamination from outside sources during the inflation/deflation of the flexible membrane 12, or during the inspection or viewing of the surface 23. Additionally, the embodiment 30, could be a hand-held unit that could be moved from part to part or the parts could be slid in and out, without the need for disassembling or the removal of the flexible foil 12.

The fluid that is pumped inside the chamber 39, could be a "smart liquid" or a conventional fluid, such as, water, Freon, mineral oil, etc. The "smart liquids" are fluids that change their optical or physical property due to external influences. An example of a "smart liquid" is a fluid containing small particles of iron that are influenced by an external magnetic field. Additionally, the fluid could also be used to heat or cool the membrane 12, or the part 22, during inspection. Furthermore, the fluid could also be used to provide thermal cycling to the part 22, to expose any latent defects or other attributes.

Figure 3:
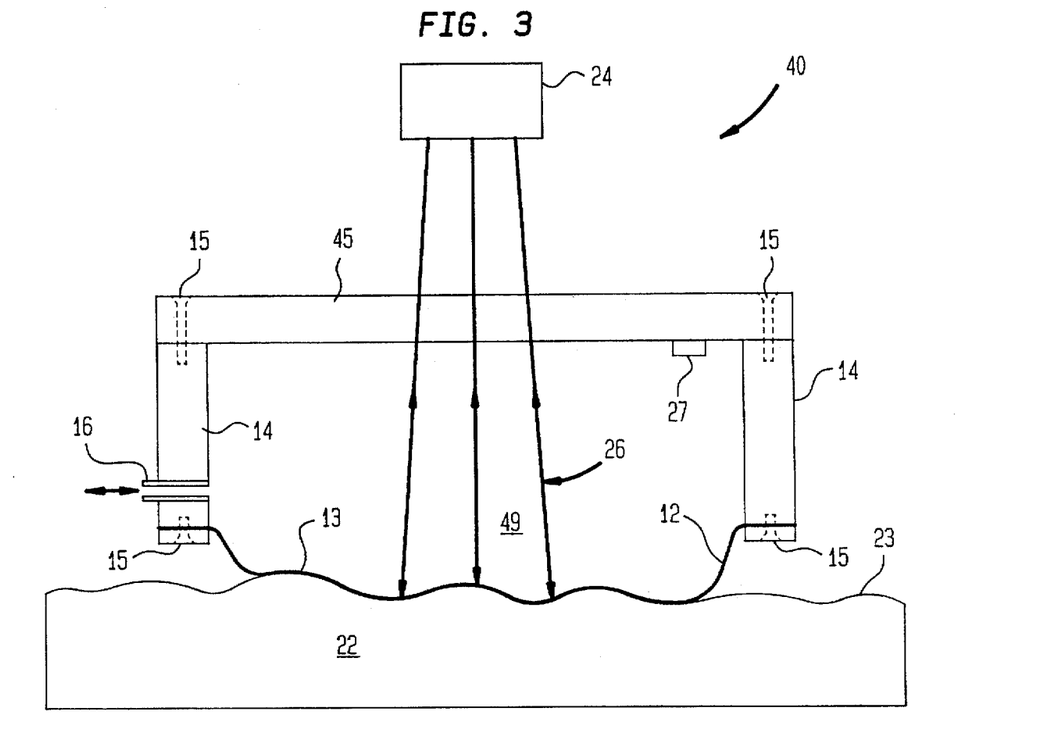
FIG. 3, illustrates yet another embodiment of the present invention.

FIG. 3, illustrates yet another embodiment 40, of the present invention. On one side the flexible foil or membrane 12, is secured to the frame or foil or membrane fixture 14, and on the opposite side a cover 45, is secured to the frame 14, using securing means 15. The cover 45, is either completely transparent or at least a portion of the cover 45, is transparent to allow for the passage and reflection of the imaging rays 26, coming from the inspection system 24, or for viewing the surface 13.

This configuration of the invention would be useful when the part or object to be inspected or viewed 22, for example, cannot be exposed to vacuum or is too large, etc. Another reason for using the embodiment 40, would be to obtain a higher resolution image or measurement of the surface 23, especially, when surface 23, is very large. In this case multiple images of the surface 23, have to be obtained in order to see the entire surface 23, at a higher resolution.

As shown in FIG. 3, the fluid-tight chamber within the frame 14, is filled and pressurized with one or more fluids, such as, air or gas, or any other suitable fluid that does not prevent or hinder the passage and reflection of the imaging rays 26. The pressurization process forces the flexible foil 12, to conformally follow the contours of the surface 23, of the object 22. Care must be taken so as not to create too much pressure in the chamber 49, that might rupture the flexible foil 12, or to create too little pressure so that the flexible foil 42, does not conform to the surface contours of the part 22.

Once the chamber 49, is properly pressurized the imaging rays 26, from the inspection system 24, are allowed to reflect off the surface 13, in case of a reflective film 12, or to reflect off the surface 23, for a clear or transparent film 12, and the image that is received is then processed as desired, for example, the information could be stored into a data base or be used to compare one surface image with an image already stored in a data base or the image could be sent to -another location for further processing.

Figure 4A:
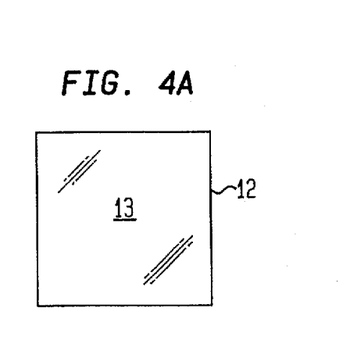
FIGS. 4A, 4B, 4C and 4D, illustrates a few possible configurations for the flexible foil or membrane that can be used with this invention.

The type of conformal foil or membrane 12, that may be used with this invention basically depends upon the needs of the application. For example, some measurement techniques require the specimen to have a reflective surface, such as, optical interferometry. In such a case, a reflective membrane 12, as shown in FIG. 4A, would be used to conformally cover the surface 23, of the part or object to be inspected 22.

A reflective membrane 12, could also be used in situations where the surface 23, of the part 22, is non-reflective and the standard reflective measurement techniques could not be used for the measurement or inspection of the part 22.

Figure 4B:
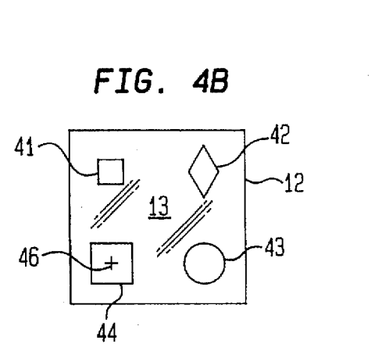

Various types of windows 41, 42, 43, 44, etc., could also be added to the reflective membrane 12, as shown in FIG. 4B. The windows 41-44, could be a physical windows cut-out of the reflective membrane 12, or they could be just areas 41-44, which are transparent in a foil 12, which is otherwise reflective or non-transparent. These one or more windows 41-44, would also allow viewing of the alignment marks or other features on the specimen, while the membrane 12, is in place over the specimen. Of course alignment or similar such marks 46, could also be placed either in the reflective or non-reflective or transparent portion of the foil or membrane 12. These marks 46, would further allow the alignment of the foil 12, to either the part 22, or to any other alignment that may be necessary to carry out the invention, for example, the alignment of the foil 12, to the base 28, or the alignment of the foil 12, to some other component during inspection or viewing, etc.

Figure 4C:
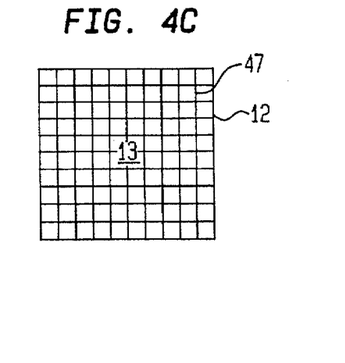

A transparent membrane or foil 12, having a grid pattern 47, printed on it could also be used with this invention. This is shown in FIG. 4C. This membrane 12, would be used when it is desired to superimpose a reference grid onto the surface 23, of the specimen or part 22. The surface 23, of the specimen or product 22, could also be viewed through the membrane 12, while the grid pattern 47, serves as a visual reference.

Figure 4D:
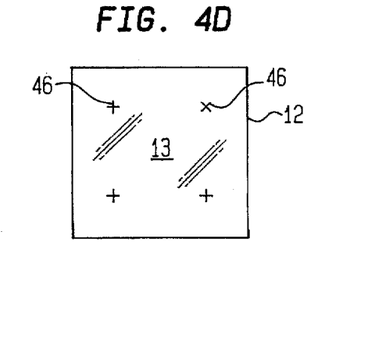

Some tools measure flatness by focussing on different points on the surface of a specimen and comparing the focus settings. To take measurements, the specimen must have optical features or markings for the tool to focus on. In such cases where the surface 23, of the specimen 22, does not have these features or markings, a transparent or opaque membrane or foil 12, with features, such as, reference markings 46, could be used, as shown in FIG. 4D. Transparent or opaque films with grid pattern 47, as shown in FIG. 4C, could also be used with markings, such as, markings 46.

EXAMPLES

The following examples are intended to further illustrate the invention and are not intended to limit the scope of the invention in any manner.

Example 1

This invention has many practical applications, for example, it could be used for the Chip Tilt Inspection and/or Measurement of a computer chip attached to single or multi-chip ceramic modules, as used by the electronics industry.

Figure 5:
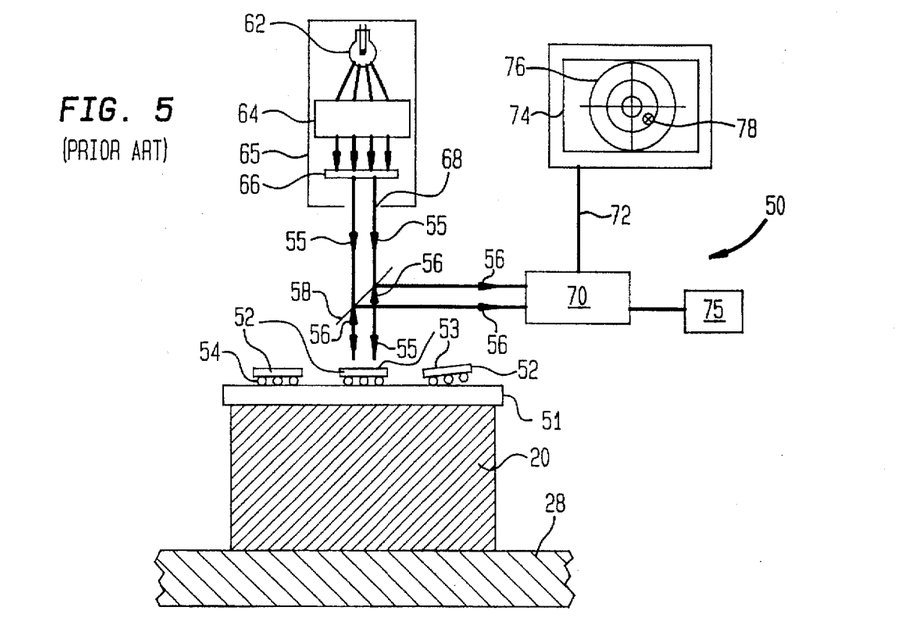
FIG. 5, illustrates one prior art method of inspection of chips.
Figure 6:
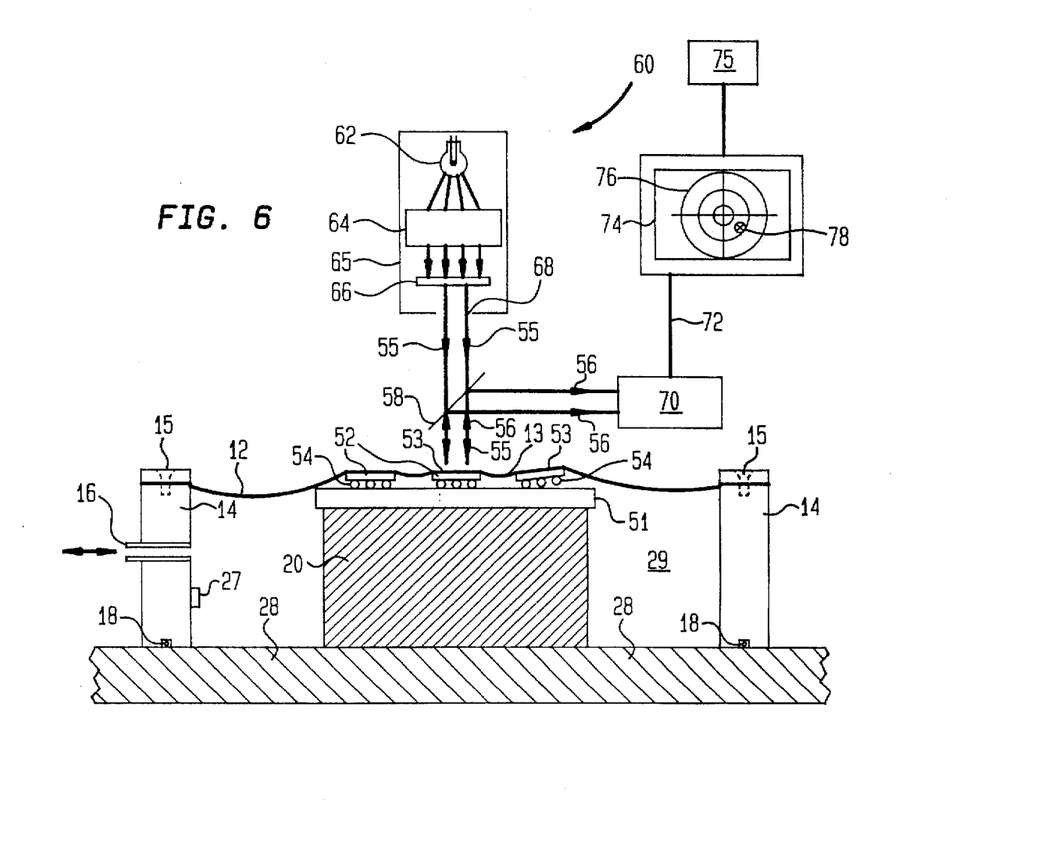
FIG. 6, illustrates one inventive method and apparatus of the inspections of chips of FIG. 5.

A prior art set-up 50, shown in FIG. 5, is typically used to measure chip tilt on multi-chip modules (MCMs). This set-up 50, uses an optical method to measure the chip tilt, relative to the bottom surface of the substrate.

A multi-chip module (MCM) substrate 51, having chips 52, is shown secured to a fixture 20, that typically sits on top of a flat base 28. Semiconductor chips 52, are typically mounted on the top surface of the substrate 51, using a plurality of solder balls or C4s 54.

A light source optical assembly 65, typically contains a light source 62, a lens assembly 64, a reticle 66, and an opening 68, for the imaging rays 55. The light source 62, is focussed through lens 64, and projected through reticle 66, creating image rays 55. The image rays 55, from the reticle 66, are projected through a beam splitting mirror 58, onto the back surface 53, of the semiconductor chip 52. The back surface 53, of the chip 52, is typically highly polished and, therefore, reflective. The image rays 55, are then reflected from the back surface 53, of the chip 52, and are projected back to the beam splitting mirror 58. From the mirror 58, the reflected image rays 56, are directed onto a solid state TV camera 70, and from there through wiring 72, it could be displayed as an image 78, on a video or TV monitor 74.

The imaging rays or incident beam 55, is aligned such that it is perpendicular to the plane of the bottom of substrate 51. If the chip 52, is tilted, relative to this plane, the incident beam 55, is deflected when it reflects from the back surface of the chip 52, as reflected beam 56. The magnitude of chip tilt is quantified by measuring the radial distance of the reticle image 78, from the center of the display screen. A calibrated pattern of concentric circles 76, is superimposed on the screen to assist in this measurement. This chip tilt measurement could be manually or automatically be monitored or stored on a data storage/retrieval or computer or controller system 75.

Example 2

The prior art technique as disclosed in Example 1, for the inspection and/or measurement of tilt in a chip can be further enhanced using the conformal membrane technique of this invention.

The measurement method of the prior art described above will only work if the back surfaces 53, of the chips 52, are reflective. In some cases, however, the back surfaces 53, of the chips 52, are not reflective, but the tilt measurements are still desired. These types of measurements can be accomplished on non-reflective chips by using the Conformal Membrane Optical Enhancement apparatus 60, as more clearly shown in FIG. 6. As before, the MCM substrate 51, is securely held on a fixture 20. The frame 14, which holds a reflective flexible membrane 12, is placed over the MCM substrate 51. The frame 14, is designed such that the reflective surface 13, of the membrane 12, rests just above the semiconductor chips 52, when the frame 14, is in place. A fluid-tight seal 18, is built into the bottom of frame 14, and is in contact with base 28. Once the frame 14, is in place, the air is partially evacuated from chamber 29, through one or more ports 16. Air pressure forces the reflective membrane 12, into intimate contact with the surface 53, of the chips 52, and causes the surface 13, of the membrane 12, to conform to the exact orientation of each chip 52. Hence, the reflective property of the membrane 12, is translated directly to the back side of each chip 52. This allows the measurement of the tilt on both reflective and non-reflective chips using the additional apparatus as shown in FIG. 5.

While the present invention has been particularly described, in conjunction with a specific preferred embodiment, it is evident that many alternatives, modifications and variations will be apparent to those skilled in the art in light of the foregoing description. It is therefore contemplated that the appended claims will embrace any such alternatives, modifications and variations as falling within the true scope and spirit of the present invention.

What is claimed is:

1. A method for the inspection and/or measurement of surfaces, comprising:
    (a) securing at least one flexible membrane to a housing, said flexible membrane having opposed surfaces, and wherein said at least one flexible membrane is in a slack state after it is secured to said housing,
    (b) at least one external means to create and maintain a pressure differential between said opposed surfaces of said at least one flexible membrane, so that at least a portion of said flexible membrane is in conformal contact with at least a portion of said surfaces to be inspected and/or measured while at least a portion of said flexible membrane not in contact with said surface to be inspected and/or measured is in a non-tense state, and wherein said external pressure does not distort the surface topology of said surface to be inspected and/or measured,
    (c) at least one inspection means to inspect at least a portion of the surface of said flexible membrane that is in conformal contact with said surfaces to be inspected while said pressure differential is maintained across said at least one flexible membrane, wherein said at least one inspection means is contained inside said housing.

2. The method of claim 1, wherein at least a portion of said housing is transparent to allow said at least one inspection means to inspect at least a portion of the surface of said flexible membrane that is in conformal contact with said surfaces to be inspected while said pressure differential is maintained across said at least one flexible membrane.

3. The method of claim 1, wherein said at least one flexible membrane is selected from a group comprising piezo electric membrane, temperature sensitive membrane, strain sensitive membrane, stress sensitive membrane, polarizing membrane, holographic membrane, colored membrane, membrane having diffraction grating, reflective membrane, transparent membrane, membrane having at least one optical coating, membrane having at least one optical filter or membrane having at least one fluid sandwiched therein.

4. The method of claim 3, wherein at least a portion of said flexible membrane has at least one physically modified surface.

5. The method of claim 4, wherein said at least one physically modified surface is formed by micro-channels or frosting or surface porosity or surface roughness or sand blasting.

6. The method of claim 1, wherein at least a portion of said at least one flexible membrane has at least one reflective surface.

7. The method of claim 1, wherein at least a portion of said at least one flexible membrane has at least one non-reflective surface.

8. The method of claim 1, wherein at least a portion of said at least one flexible membrane is transparent.

9. The method of claim 1, wherein at least a portion of said at least one flexible membrane has at least one grid pattern.

10. The method of claim 1, wherein said at least one inspection means is an opto-electronic inspection means.

11. The method of claim 1, wherein said at least one flexible membrane is secured to the peripheral edges of said housing by said at least one securing means.

12. The method of claim 1, wherein said housing comprises at least one sensor means for sensing temperature or pressure or both of the inside of said housing.

13. The method of claim 1, wherein said pressure differential is maintained across said at least one flexible membrane by the introduction of at least one fluid on at least one side of said flexible membrane.

14. The method of claim 13, wherein said fluid is selected from a group consisting of gas, such as, air, helium, nitrogen, or a liquid, such as, mineral oil, Freon, water.

15. The method of claim 13, wherein at least a portion of said fluid is used to provide thermal cycling to at least a portion of said flexible membrane.

16. The method of claim 13, wherein at least a portion of said fluid is used to provide thermal cycling to at least a portion of said surface to be inspected.

17. A method for the inspection and/or measurement of surfaces, comprising:
    (a) securing at least one flexible membrane to a housing, said flexible membrane having opposed surfaces, and wherein said at least one flexible membrane is in a slack state after it is secured to said housing,
    (b) at least one external means to create and maintain a pressure differential between said opposed surfaces of said at least one flexible membrane, so that at least a portion of said flexible membrane is in conformal contact with at least a portion of said surfaces to be inspected and/or measured while at least a portion of said flexible membrane not in contact with said surface to be inspected and/or measured is in a non-tense state, and wherein said external pressure does not distort the surface topology of said surface to be inspected and/or measured, (c) at least one inspection means to inspect at least a portion of the surface of said flexible membrane that is in conformal contact with said surfaces to be inspected while said pressure differential is maintained across said at least one flexible membrane, wherein said pressure differential is maintained across said at least one flexible membrane by the introduction of at least one fluid on at least one side of said flexible membrane.

18. The method of claim 17, wherein said fluid is selected from a group consisting of gas, such as, air, helium, nitrogen, or a liquid, such as, mineral oil, Freon, water.

19. The method of claim 17, wherein at least a portion of said fluid is used to provide thermal cycling to at least a portion of said flexible membrane.

20. The method of claim 17, wherein at least a portion of said fluid is used to provide thermal cycling to at least a portion of said surface to be inspected.

21. An apparatus for the inspection and/or measurement of surfaces, comprising:

(a) at least one housing having at least one flexible membrane secured to said housing, said flexible membrane having opposed surfaces, and wherein said at least one flexible membrane is in a slack state after it is secured to said housing, (b) at least one external means to create and maintain a pressure differential between said opposed surfaces of said at least one flexible membrane, so that at least a portion of said flexible membrane is in conformal contact with at least a portion of said surfaces to be inspected and/or measured while at least a portion of said flexible membrane not in contact with said surface to be inspected and/or measured is in a non-tense state, and wherein said external pressure does not distort the surface topology of said surface to be inspected and/or measured, (c) at least one inspection means to inspect at least a portion of the surface of said flexible membrane that is in conformal contact with said surface to be inspected while said pressure differential is maintained across said at least one flexible membrane, wherein said at least one inspection means is contained inside said housing.

22. The apparatus of claim 21, wherein at least a portion of said housing is transparent to allow said at least one inspection means to inspect at least a portion of the surface of said flexible membrane that is in conformal contact with said surfaces to be inspected while said pressure differential is maintained across said at least one flexible membrane.

23. The apparatus of claim 21, wherein said at least one flexible membrane is selected from a group comprising piezo electric membrane, temperature sensitive membrane, strain sensitive membrane, stress sensitive membrane, polarizing membrane, holographic membrane, colored membrane, membrane having diffraction grating, reflective membrane, transparent membrane, membrane having at least one optical coating, membrane having at least one optical filter or membrane having at least one fluid sandwiched therein.

24. The apparatus of claim 23, wherein at least a portion of said flexible membrane has at least one physically modified surface.

25. The apparatus of claim 24, wherein said at least one physically modified surface is formed by micro-channels or frosting or surface porosity or surface roughness or sand blasting.

26. The apparatus of claim 21, wherein at least a portion of said at least one flexible membrane has at least one reflective surface.

27. The apparatus of claim 21, wherein at least a portion of said at least one flexible membrane has at least one non-reflective surface.

28. The apparatus of claim 21, wherein at least a portion of said at least one flexible membrane is transparent.

29. The apparatus of claim 21, wherein at least a portion of said at least one flexible membrane has at least one grid pattern.

30. The apparatus of claim 21, wherein said at least one inspection means is an opto-electronic inspection means.

31. The apparatus of claim 21, wherein said at least one flexible membrane is secured to the peripheral edges of said housing by said at least one securing means.

32. The apparatus of claim 21, wherein said housing comprises at least one sensor means for sensing temperature or pressure or both of the inside of said housing.

33. The apparatus of claim 21, wherein said pressure differential is maintained across said at least one flexible membrane by the introduction of at least one fluid on at least one side of said flexible membrane.

34. The apparatus of claim 33, wherein said at least one fluid is selected from a group consisting of gas, such as, air, helium, nitrogen, or a liquid, such as, mineral oil, Freon, water.

35. The apparatus of claim 33, wherein at least a portion of said fluid is used to provide thermal cycling to at least a portion of said flexible membrane.

36. The apparatus of claim 33, wherein at least a portion of said fluid is used to provide thermal cycling to at least a portion of said surface to be inspected.

37. An apparatus for the inspection and/or measurement of surfaces, comprising:

(a) at least one housing having at least one flexible membrane secured to said housing, said flexible membrane having opposed surfaces, and wherein said at least one flexible membrane is in a slack state after it is secured to said housing, (b) at least one external means to create and maintain a pressure differential between said opposed surfaces of said at least one flexible membrane, so that at least a portion of said flexible membrane is in conformal contact with at least a portion of said surfaces to be inspected and/or measured while at least a portion of said flexible membrane not in contact with said surface to be inspected and/or measured is in a non-tense state, and wherein said external pressure does not distort the surface topology of said surface to be inspected and/or measured, (c) at least one inspection means to inspect at least a portion of the surface of said flexible membrane that is in conformal contact with said surface to be inspected while said pressure differential is maintained across said at least one flexible membrane, wherein said pressure differential is maintained across said at least one flexible membrane by the introduction of at least one fluid on at least one side of said flexible membrane.

38. The apparatus of claim 37, wherein said at least one fluid is selected from a group consisting of gas, such as, air, helium, nitrogen, or a liquid, such as, mineral oil, Freon, water.

39. The apparatus of claim 37, wherein at least a portion of said fluid is used to provide thermal cycling to at least a portion of said flexible membrane.

40. The apparatus of claim 37, wherein at least a portion of said fluid is used to provide thermal cycling to at least a portion of said surface to be inspected.

41. An apparatus for the inspection and/or measurement of surfaces, comprising:
   (a) at least one housing having at least one flexible membrane secured to said housing, said flexible membrane having opposed surfaces, and wherein said at least one flexible membrane is in a slack state after it is secured to said housing,
   (b) at least one external means to create and maintain a pressure differential between said opposed surfaces of said at least one flexible membrane, so that at least a portion of said flexible membrane is in conformal contact with at least a portion of said surfaces to be inspected and/or measured while at least a portion of said flexible membrane not in contact with said surface to be inspected and/or measured is in a non-tense state, and wherein said external pressure does not distort the surface topology of said surface to be inspected and/or measured,
   (c) at least one inspection means to inspect at least a portion of the surface of said flexible membrane that is in conformal contact with said surface to be inspected while said pressure differential is maintained across said at least one flexible membrane, wherein said at least one flexible membrane has at least one alignment marking on it.

42. The apparatus of claim 41, wherein said at least one inspection means is contained inside said housing.

43. The apparatus of claim 41, wherein at least a portion of said housing is transparent to allow said at least one inspection means to inspect at least a portion of the surface of said flexible membrane that is in conformal contact with said surfaces to be inspected while said pressure differential is maintained across said at least one flexible membrane.

44. The apparatus of claim 41, wherein said at least one flexible membrane is selected from a group comprising piezo electric membrane, temperature sensitive membrane, strain sensitive membrane, stress sensitive membrane, polarizing membrane, holographic membrane, colored membrane, membrane having diffraction grating, reflective membrane, transparent membrane, membrane having at least one optical coating, membrane having at least one optical filter or membrane having at least one fluid sandwiched therein.

45. The apparatus of claim 44, wherein at least a portion of said flexible membrane has at least one physically modified surface.

46. The apparatus of claim 45, wherein said at least one physically modified surface is formed by micro-channels or frosting or surface porosity or surface roughness or sand blasting.

47. The apparatus of claim 41, wherein at least a portion of said at least one flexible membrane has at least one reflective surface.

48. The apparatus of claim 41, wherein at least a portion of said at least one flexible membrane has at least one non-reflective surface.

49. The apparatus of claim 41, wherein at least a portion of said at least one flexible membrane is transparent.

50. The apparatus of claim 41, wherein at least a portion of said at least one flexible membrane has at least one grid pattern.

51. The apparatus of claim 41, wherein said at least one inspection means is an opto-electronic inspection means.

52. The apparatus of claim 41, wherein said at least one flexible membrane is secured to the peripheral edges of said housing by said at least one securing means.

53. The apparatus of claim 41, wherein said housing comprises at least one sensor means for sensing temperature or pressure or both of the inside of said housing.

54. The apparatus of claim 41, wherein said pressure differential is maintained across said at least one flexible membrane by the introduction of at least one fluid on at least one side of said flexible membrane.

55. The apparatus of claim 54, wherein at least a portion of said fluid is used to provide thermal cycling to at least a portion of said flexible membrane.

56. The apparatus of claim 54, wherein at least a portion of said fluid is used to provide thermal cycling to at least a portion of said surface to be inspected.

57. The apparatus of claim 54, wherein said at least one fluid is selected from a group consisting of gas, such as, air, helium, nitrogen, or a liquid, such as, mineral oil, Freon, water.

58. A method for the inspection and/or measurement of surfaces, comprising:
   (a) securing at least one flexible membrane to a housing, said flexible membrane having opposed surfaces, and wherein said at least one flexible membrane is in a slack state after it is secured to said housing,
   (b) at least one external means to create and maintain a pressure differential between said opposed surfaces of said at least one flexible membrane, so that at least a portion of said flexible membrane is in conformal contact with at least a portion of said surfaces to be inspected and/or measured while at least a portion of said flexible membrane not in contact with said surface to be inspected and/or measured is in a non-tense state, and wherein said external pressure does not distort the surface topology of said surface to be inspected and/or measured,
   (c) at least one inspection means to inspect at least a portion of the surface of said flexible membrane that is in conformal contact with said surfaces to be inspected while said pressure differential is maintained across said at least one flexible membrane, wherein said at least one flexible membrane has at least one alignment marking on it.

59. The method of claim 58, wherein said at least one inspection means is contained inside said housing.

60. The method of claim 58, wherein at least a portion of said housing is transparent to allow said at least one inspection means to inspect at least a portion of the surface of said flexible membrane that is in conformal contact with said surfaces to be inspected while said pressure differential is maintained across said at least one flexible membrane.

61. The method of claim 58, wherein said at least one flexible membrane is selected from a group comprising piezo electric membrane, temperature sensitive membrane, strain sensitive membrane, stress sensitive membrane, polarizing membrane, holographic membrane, colored membrane, membrane having diffraction grating, reflective membrane, transparent membrane, membrane having at least one optical coating, membrane having at least one optical filter or membrane having at least one fluid sandwiched therein.

62. The method of claim 61, wherein at least a portion of said flexible membrane has at least one physically modified surface.

63. The method of claim 62, wherein said at least one physically modified surface is formed by micro-channels or frosting or surface porosity or surface roughness or sand blasting.

64. The method of claim 58, wherein at least a portion of said at least one flexible membrane has at least one reflective surface.

65. The method of claim 58, wherein at least a portion of said at least one flexible membrane has at least one non-reflective surface.

66. The method of claim 58, wherein at least a portion of said at least one flexible membrane is transparent.

67. The method of claim 58, wherein at least a portion of said at least one flexible membrane has at least one grid pattern.

68. The method of claim 58, wherein said at least one inspection means is an opto-electronic inspection means.

69. The method of claim 58, wherein said at least one flexible membrane is secured to the peripheral edges of said housing by said at least one securing means.

70. The method of claim 58, wherein said housing comprises at least one sensor means for sensing temperature or pressure or both of the inside of said housing.

71. The method of claim 58, wherein said pressure differential is maintained across said at least one flexible membrane by the introduction of at least one fluid on at least one side of said flexible membrane.

72. The method of claim 71, wherein said fluid is selected from a group consisting of gas, such as, air, helium, nitrogen, or a liquid, such as, mineral oil, Freon, water.

73. The method of claim 71, wherein at least a portion of said fluid is used to provide thermal cycling to at least a portion of said flexible membrane.

74. The method of claim 71, wherein at least a portion of said fluid is used to provide thermal cycling to at least a portion of said surface to be inspected.

* * * * *